US011179274B2

(12) United States Patent
Vinton

(10) Patent No.: US 11,179,274 B2
(45) Date of Patent: *Nov. 23, 2021

(54) OXYGEN DISTRIBUTOR

(71) Applicant: Inotec AMD Limited, Cambridge (GB)

(72) Inventor: Melvin Frederick Vinton, Cambridge (GB)

(73) Assignee: Inotec AMD Limited, Cambridge (GB)

( * ) Notice: Subject to any disclaimer, the term of this patent is extended or adjusted under 35 U.S.C. 154(b) by 424 days.

This patent is subject to a terminal disclaimer.

(21) Appl. No.: 16/138,840

(22) Filed: Sep. 21, 2018

(65) Prior Publication Data

US 2019/0030307 A1    Jan. 31, 2019

Related U.S. Application Data

(63) Continuation of application No. 14/394,729, filed as application No. PCT/GB2013/050980 on Apr. 18, 2013, now Pat. No. 10,080,850.

(30) Foreign Application Priority Data

Apr. 19, 2012 (GB) ..................................... 1206907
May 1, 2012 (GB) ..................................... 1207571

(51) Int. Cl.
*A61M 35/00* (2006.01)
*A61M 1/00* (2006.01)
*A61F 13/00* (2006.01)
*A61G 10/02* (2006.01)
*A61H 33/14* (2006.01)
*A61M 13/00* (2006.01)
(Continued)

(52) U.S. Cl.
CPC .. *A61F 13/00068* (2013.01); *A61F 13/00042* (2013.01); *A61G 10/026* (2013.01); *A61H 33/14* (2013.01); *A61M 1/85* (2021.05); *A61M 13/003* (2013.01); *A61M 35/30* (2019.05); *A61F 2013/00093* (2013.01); *A61F 2013/00268* (2013.01); *A61M 2202/0208* (2013.01); *A61M 2205/3303* (2013.01)

(58) Field of Classification Search
CPC ........ A61M 35/00; A61M 1/00; A61M 27/00; A61M 2202/0208; A61M 2205/3303; A61F 13/00; A61F 13/02; A61F 13/00042; A61F 2013/00093; A61F 2013/00268; A61G 10/026; A61H 33/14
See application file for complete search history.

(56) References Cited

U.S. PATENT DOCUMENTS

2003/0212357 A1* 11/2003 Pace ................... A61M 1/0052
602/41
2012/0059301 A1* 3/2012 Franklin ........... A61F 13/00051
602/48

FOREIGN PATENT DOCUMENTS

CN    101417161 A  * 10/2007
GB    2470358      *  5/2009

* cited by examiner

*Primary Examiner* — Tatyana Zalukaeva
*Assistant Examiner* — Ilya Y Treyger
(74) *Attorney, Agent, or Firm* — Squire Patton Boggs (US) LLP

(57) ABSTRACT

An oxygen distributor (1) positionable, in use, in a wound for supplying oxygen to the wound has an oxygen delivery area (17) for, in use, receiving a supply of oxygen. At least one tube (19A) extends from the oxygen delivery area, having a tube wall with an oxygen-permeable, liquid-impermeable section. Oxygen delivered to the oxygen delivery area can flow away from the oxygen delivery area along the, or each, tube.

20 Claims, 4 Drawing Sheets

(51) Int. Cl.
*A61M 27/00* (2006.01)
*A61F 13/02* (2006.01)

OXYGEN DISTRIBUTOR

This invention relates to a hyperbaric distributor for delivering oxygen or other therapeutic gases to a wound.

BACKGROUND TO THE INVENTION

It is known that a supply of oxygen to a wound promotes healing and reduces scarring. It is believed that increased oxygen content of tissue fluids promotes metabolism and repair of damaged tissues.

It is also known that if a wound produces a large amount of exudate, such as if a wound becomes chronic and non-healing or when infection becomes established, the healing process can be slowed down and can lead to maceration of the surrounding skin. Such wounds can produce large volumes of exudate and this can cause significant problems in wound treatment.

SUMMARY OF INVENTION

The invention provides an oxygen distributor or oxygen distributing apparatus as defined in the appended independent claims to which reference should now be made. Advantageous or preferred features are set forth in dependent claims.

Accordingly, the invention may thus provide an oxygen distributor, positionable, in use, in a wound for supplying oxygen to a surface of the wound, comprising:
- an oxygen delivery area or portion for, in use, receiving a supply of oxygen;
- at least one tube or duct extending from the oxygen delivery area having a tube wall, at least a section or portion of the tube wall being oxygen-permeable and liquid-impermeable;
- in which oxygen delivered to the oxygen delivery area can flow away from the oxygen delivery area along the or each tube and permeate through the oxygen-permeable, liquid-impermeable portion of the tube wall.

Thus, advantageously, the tube or tubes of the oxygen distributor may allow supply of oxygen to a wound without covering the wound and while allowing exudate to flow freely away from the wound.

It is desirable to be able to cut the oxygen distributor so as to change its size. This may advantageously reduce the number of sizes of distributor that a hospital or medical practitioner may need to stock, as the size of a distributor may be reduced by cutting to fit within a particular wound.

Restricting the oxygen to flow along a tube or tubes may make the oxygen distributor amenable to cutting, as cutting across a tube may only expose a small section of the internal space of the distributor and may thus reduce the potential for exudate to leak into the distributor and for significant amounts of oxygen to escape. The presence of tubes may also allow greater control of where oxygen is distributed within a wound. Spacing the tubes from each other may allow oxygen distributing areas to be spaced from each other. This may advantageously increase flexibility when cutting.

It is intended, in use, that a dressing such as a standard absorbent dressing and/or a compression bandage may be placed over the distributor to soak up and retain any exudate produced. It is also preferable that the distributor does not have adhesive for adhering to or around the wound. Preferably, the distributor is to be positioned within a wound and that the wound, and the distributor, is covered by a dressing.

Preferably the distributor comprises a plurality of tubes extending or emanating from the oxygen delivery area, such that the oxygen delivery area comprises or forms a manifold or a hub of the distributor.

The oxygen distributor is preferably in the form of a web or a mesh and thus may comprise a network of tubes. Advantageously, this may deliver oxygen to different parts of the wound. For example, the distributor may comprise one or more tubes which are coupled to or extend from the tube or at least one of the tubes extending from the oxygen delivery area, so that oxygen may flow from the oxygen delivery area to all of the tubes of the distributor.

The tubes extending from the oxygen delivery area may be substantially straight and/or may extend radially and/or may be curved. The oxygen delivery area is preferably located centrally in the oxygen distributor. This may mean that the concentration of oxygen or the gas pressure is greatest at the centre and is lowest at the periphery of the distributor, or web. Trimming or cutting the distributor at its periphery, or at a point spaced from the oxygen delivery area, to reduce the size of the distributor may thus negate excessive oxygen loss.

In a preferred embodiment, the oxygen delivery area may comprise a delivery tube. The delivery tube may be straight, or may be not straight, or may be in the shape of a ring or a portion of a ring, or may be formed into a circular, elliptical, rectangular, square or similar shape. The tube or tubes extending from the oxygen delivery area may then extend from different positions around or along the length of the delivery tube.

An open aperture may be surrounded by a ring-like delivery tube, which may permit, in use, flow of exudate away from the wound.

Preferably, the oxygen delivery area comprises a wall and a portion or section of the wall is oxygen-permeable and liquid-impermeable, to allow oxygen to diffuse from the oxygen delivery area to an adjacent region of a wound.

Preferably, the tube or tubes extending from the oxygen delivery area extend to a peripheral edge of the distributor. If the distributor is substantially circular or rectangular in shape, for example, the tube or tubes extending from the oxygen delivery area may extend to an outside edge of the circle or rectangle.

The distributor may comprise one or more branching tubes having a tube wall, the tube wall having an oxygen-permeable, liquid-impermeable section or portion, the or each branching tube branching from, or connected to, the tube or at least one of the tubes extending from the oxygen delivery area.

Preferably, a branching tube branches from a tube or tubes extending from the oxygen delivery area. Preferably, a branching tube is connected to an end of a tube or tubes extending from the oxygen delivery area, which is spaced from or furthest from the oxygen delivery area. In a preferred embodiment, the branching tube or at least one of the branching tubes extends around or along a section of the perimeter of the distributor. If the distributor is substantially circular, for example, the or each branching tube may extend around a section of the circumferential edge. The or each branching tube may extend substantially perpendicularly with respect to the or each tube extending from the oxygen delivery area. The branching tube may form a continuous ring. The branching tube or at least one of the branching tubes may have further tubes connected to it or extending from it.

Preferably, the only tube or tubes between the oxygen delivery area and the periphery of the web may be the tube or tubes extending from the oxygen delivery area. Optionally, no other tubes may branch from the tubes extending from the oxygen delivery area other than the or each branching tube located at the periphery or perimeter of the distributor. Thus, each tube extending from the oxygen delivery area may have only two junction points: a first junction point at which it is connected to the oxygen delivery area; and a second junction point at which it is connected to one or more of the branching tubes.

Preferably, the distributor comprises a plurality of independent sub-networks of tubes emanating from the oxygen-delivery area. Thus, tubes of one sub-network may not be interconnected with tubes of another sub-network. Each sub-network may comprise at least one of the tubes extending from the oxygen delivery area. In one example, each sub-network comprises a single tube extending from the oxygen delivery area. The or each sub-network may also comprise one or more branching tubes which branch from the tube or tubes extending from the oxygen delivery area. Thus, excluding the oxygen delivery area, a first tube joined to the oxygen delivery area and any tubes deriving or extending from the first tube, may not be interconnected with a second tube connected to the oxygen delivery area or any other tubes deriving or extending from the second tube. Thus, the arrangement of tubes from the oxygen delivery area may thus resemble the arrangement of branches from the trunk of a tree. The distributor may then advantageously be cuttable such that only one sub-network is affected.

Preferably, each tube, or at least some of the tubes of the distributor, comprise(s) a tube wall portion which is oxygen-permeable and liquid-impermeable. Preferably, the remaining portion of each tube wall which is not oxygen-permeable and liquid-impermeable is oxygen-impermeable and liquid-impermeable. Preferably, the portion of the tube wall which is oxygen-permeable and liquid-impermeable is for facing the wound, in use. Preferably, the portion of the tube wall which is oxygen-impermeable and liquid-impermeable is for facing away from the wound, in use.

Advantageously, all tube walls of the distributor may be liquid-impermeable, in order to prevent any flow of exudate from the wound into the tubes of the distributor. Advantageously, at least some portions of the tube walls which face a wound, in use, may be oxygen-permeable, or gas-permeable, to allow oxygen delivered to the distributor to diffuse or permeate out of the distributor to the wound. Other portions of the tube walls, such as at least some portions which face away from the wound, in use, may be oxygen-impermeable, or gas-impermeable, so that oxygen delivered to the distributor diffuses or permeates out of the distributor only towards the wound. In a further aspect of the invention, however, at least some portions of the tube walls which face away from the wound, in use, may also be oxygen-permeable, or gas-permeable. As the tubes of the distributor are advantageously of small diameter, oxygen diffusing out of a tube wall portion facing away from a wound, and beneath a dressing, may still be delivered close enough to the wound to have a beneficial therapeutic effect. Therefore, in a still further aspect of the invention, substantially all of the tube walls of the distributor may be liquid-impermeable and oxygen-permeable, or gas-permeable. The tube walls may then all be made of the same material, for example, simplifying the fabrication of the distributor.

A general reference to "tube" or "tubes" herein, may include any tube in the distributor which comprises a wall with an oxygen-permeable, liquid-impermeable section and may thus include, for example, the or each tube extending from the oxygen delivery area, the or each branching tube (if present) and the delivery tube or tubes of the oxygen delivery area (if present). It may include any further tube or tubes connected to a branching tube and thus may include any tube which derives from the or each tube extending from the oxygen delivery area.

In a preferred embodiment, at least a portion of the distributor may be fabricated by joining an oxygen-permeable, liquid-impermeable layer, to an oxygen-impermeable, liquid-impermeable layer. The oxygen-permeable, liquid-impermeable and oxygen-impermeable, liquid-impermeable layers are typically made of suitable flexible plastics materials. Each layer is typically of thickness 0.01 to 1 millimeter (mm), preferably 0.05 to 1 mm. The layers may be sealed or joined together in such a way as to define one or more of the tubes of the distributor.

In this preferred embodiment, the oxygen distributor may be seen as comprising one or more tracks and each track may comprise sealed-together sections of the oxygen-permeable, liquid-impermeable layer and oxygen-impermeable, liquid-impermeable layer. One or more of the tubes may be defined in each track between the oxygen-permeable, liquid-impermeable layer, and the oxygen-impermeable, liquid-impermeable layer. Each tube may be defined between sealed edges or sealed sides in a track. Preferably, each track comprises one tube, or may comprise more than one tube.

If the distributor is in the form of a web, there may be an interconnected network of tracks and a network of the tubes may be defined in the network of tracks. Each track in the network may form a strand or filament of the web. Preferably, if there is a plurality of tracks, each track is joined to one or more other tracks so that oxygen carried along the tracks in the tubes can flow from one track to another.

In a preferred embodiment, each track defines only one tube across its width. In other words, each track may preferably not have two or more tubes defined side by side within it. This may advantageously maximise the open area between different tracks to permit flow of exudate away from the wound, through the distributor.

The oxygen-permeable, liquid-impermeable layer and the oxygen-impermeable, liquid-impermeable layer may be secured together by means of welding, such as sonic welding, or induction heating, or in any other way.

Preferably, the distributor comprises a track in which the oxygen delivery area is defined. Preferably, this is an inner, central ring-like track. The ring-like track may be, for example, circular, elliptical or rectangular. An inner edge of the ring-like track may define an opening or aperture for exudate flow. Preferably, there are radial tracks or spokes emanating or extending from the central track. There may also be an outer, ring-like track outside of the radial tracks. The outer ring-like track may define the perimeter of the distributor or the web, and may be spaced from the oxygen delivery area by the radial tracks.

The oxygen delivery area, for example the ring-like tube, may be defined in the central ring-like track. One or more of the radial tracks may define one or more of the tubes extending from the oxygen delivery area. Preferably, the outer-ring-like track defines one or more of the branching tubes. Parts of one or more of the tracks may be sealed across their entire width to define tubes with closed or blind ends. The sealed parts of the tracks may, for example, separate a tube of one sub-network from a tube of a neighbouring sub-network. For example, the peripheral track may be sealed at specific parts or points between adjacent branching tubes. Advantageously, this may mechanically join the blind-ended tubes, to provide physical support, while providing an opportunity for cutting the distributor such that only one sub-network is affected, leaving remaining sub-networks intact. For example, lateral cuts may then be made across the outer track between adjacent branching tubes without cutting across any branching tube.

The distributor may comprise an oxygen delivery means. Preferably, the oxygen delivery means may be arranged to supply oxygen or air or other therapeutic gas to the oxygen delivery area. Typically the oxygen delivery means comprises a conduit and a coupling means for connecting the conduit to an oxygen source such as an electrolytic oxygen generator, oxygen cylinder, compressor or the like. One end of the tube may be attached permanently (for example by sealing) to the oxygen delivery area. Alternatively, the oxygen delivery means may be releasably connectable to the oxygen delivery area.

Preferably, the oxygen delivery means oxygen source is configured to deliver oxygen to the distributor at a rate of up to 30 ml/hour, preferably from 10 to 20 ml/hour. In a preferred embodiment, the oxygen is delivered at a slightly hyperbaric pressure, for example at about 50 millibar (mbar) above atmospheric pressure.

Preferably, the or each tube comprises or contains a porous material, such as an open cell foam. The porous material may be distributed throughout the or each tube. This may advantageously keep the tubes open and able to conduct oxygen even if pressure is placed on top of the distributor, for example by the application of a compression bandage over the distributor. Alternatively, at least a portion of the tube walls of the distributor may be sufficiently rigid or may be reinforced to prevent the or each tube from collapsing.

If there is a plurality of tubes extending from the oxygen delivery area, there are preferably regions between the tubes extending from the oxygen delivery area or the tracks in which these tubes are defined, for allowing, in use, exudate from the wound to flow away from the wound. Large openings or apertures for exudate may be defined between the tubes, or defined between the tracks, such as between edges of the tracks. The openings are preferably substantially bound or surrounded by one or more of the tracks and/or the tubes. This may create apertures that are, for example, substantially elliptical, rectangular or trapezoid in shape. For example, apertures may be defined between an inner ring-like track, radial tracks and (optionally) an outer, ring-like track.

However, the openings may not be completely surrounded by the tracks and/or the tubes. For example, the openings may be defined between two tracks or two tubes, such as two tracks or tubes extending radially from the oxygen delivery area.

Advantageously, the tubes may be of such a dimension and so arranged, that if they are cut across their width to expose an open end, in use, exudate cannot substantially enter the tubes. It has been found that if the tubes are sufficiently small, exudate may actually seal the ends of cut tubes and prevent or reduce oxygen being lost from their ends. For example, each tube may have a maximum width or average width of less than or equal to 10, 8, 6, 5, 4, 3, 2 or 1 millimeter (mm). Preferably, each tube has a maximum height or average height of less than 5, 4, 3, 2 or 1 mm. Preferably, the maximum or average cross-sectional area of each tube is less than or equal to 25, 20, 15, 10, 5, 2 or 1 mm$^2$. In a further aspect the invention may advantageously provide a method for cutting an oxygen distributor comprising these features and related features described in this document.

Preferably, the length of each tube is at least 3, 5 or 7 times greater than its average or maximum width.

Preferably, an inner surface of a tube, and any material within the tube such as open cell foam, is hydrophobic, to prevent or reduce wetting, or wicking, exudate.

Preventing exudate from entering the tubes is important to avoid a risk of infection.

In a preferred embodiment, the distributor comprises a cutting area which defines an area of the distributor outside of the oxygen delivery area.

Preferably, the cutting area is so arranged that if a single, straight cut is made anywhere across the cutting area to reduce the area of the distributor, no more than five, preferably no more than four, three, two or one tube(s), are cut across their width. Cutting across the width of a tube may mean across the entire width, from one side or edge of the tube to the other, such that a portion of the tube is removed. The cut need not be precisely perpendicular to the longitudinal axis of the tube but is preferably at an angle of more than 10°, or 20°, or 30°, to the longitudinal axis of the tube.

Preferably, the cutting area is so arranged that if a single, straight cut is made anywhere across the cutting area to reduce the area of the distributor, the surface area of a cut section, or cut end, of any of the tubes which have been cut is less than or equal to 25, 20, 15, 10, 5, 2 or 1 mm$^2$.

Preferably, the cutting area is arranged such that if a single, straight cut is made anywhere across the cutting area to reduce the area of the distributor, no more than three, and preferably no more than two or one, of the tubes extending from the oxygen delivery area are cut across their width.

Preferably, the cutting area is arranged such that if a single, straight cut is made across a portion of the cutting area comprising one or more of the tubes extending from the oxygen delivery area, to reduce the area of the distributor, the one or more of the tubes extending from the oxygen delivery area is cut across its width.

The distributor may be considered as comprising an oxygen distribution portion, which consists of the portion of the distributor which is placed in a wound, in use, for distributing oxygen to the wound, and an oxygen delivery means, which extends from the oxygen distribution portion for coupling to an oxygen supply. In use, the oxygen distribution portion may thus be positioned in a wound and covered by a dressing and the oxygen delivery means, for example comprising an oxygen delivery conduit, may protrude from beneath the dressing for coupling to the oxygen supply.

The oxygen distribution portion may thus comprise or consist of the oxygen delivery area and the tubes, such as the tube or tubes extending from the oxygen delivery area and any tubes deriving from the tube or tubes extending from the oxygen delivery area, such as the branching tubes (if present). The apertures for the flow of exudate are therefore apertures extending through the oxygen distribution portion.

Advantageously, the total area of the apertures for the flow of exudate away from the wound through the distributor should be as large as possible. Therefore, in a preferred embodiment, the area, in plan, of the oxygen distribution portion is less than or equal to 50% of the total area of the distributor, the remainder of the area of the distributor being the area of the apertures. Preferably, the area of the oxygen distribution portion is less than or equal to 40, 30, 20 or 10% of the total area of the distributor. The area of the oxygen distribution portion may be the area of a wound underneath or covered by the oxygen distribution portion, in use. The total area of the distributor may be the total area underneath the distributor, in use. The total area may be the area defined by, or within, a peripheral edge of the distributor, or the perimeter of the distributor (whether or not the distributor comprises a peripheral tube, or track). For example, if the distributor is substantially circular, the area may be defined, or at least partially defined, by the outer edge of the circle. The total area thus includes the apertures for exudate to flow through the distributor, which are advantageously as large as possible.

In a preferred embodiment, the area, in plan, of the oxygen distribution portion is less than the total area of the openings or apertures for exudate.

The distributor may or may not comprise a peripheral tube or track, but in either case its area may be evaluated as follows.

If the oxygen distribution portion fits within, or is placed within, a rectangle that has a length equivalent to a maximum length across the oxygen distribution portion and a width equivalent to a maximum width across the oxygen distribution portion, the area of the rectangle is the area of the distributor. The area covered by the oxygen distribution portion is then preferably less than or equal to 50% of the area of the rectangle. Even more preferably, the area may be less than or equal to 40, 30, 20 or 10% of the area of the rectangle.

Alternatively, if the oxygen distribution portion fits within, or is placed within, a circle or other similar closed shape with a diameter or lateral dimension equal to the maximum distance across the oxygen distribution portion, the area of the circle or closed shape is the area of the distributor. It is then preferable that the area within the circle or shape which is covered by the oxygen distribution portion is less than or equal to 50% of the area of the circle or shape. Even more preferably, the area is less than or equal to 40, 30, 20 or 10% of the area of the circle or shape.

For evaluating the area of the oxygen distribution portion a suitable closed shape may be a straight-sided polygon linking radially-outermost points of the oxygen distribution portion with straight lines. If the oxygen distribution portion comprises a peripheral tube or track, its area is the area bounded by the peripheral tube or track.

Although it is most preferred that the oxygen distributor distributes oxygen to a wound, other therapeutic gases could also be delivered using the distributor. Thus, the distributor may have more general application as a gas distributor, such as a gas distribution web. The gas distributor may thus have a gas-delivery area with a tube extending from the gas delivery area. The tube may thus have a wall, a portion of the wall being gas-permeable and liquid-impermeable.

SPECIFIC DESCRIPTION OF THE PREFERRED EMBODIMENT

An embodiment of the invention will now be described, by way of example, and with reference to the accompanying drawings in which.

Figure 1:
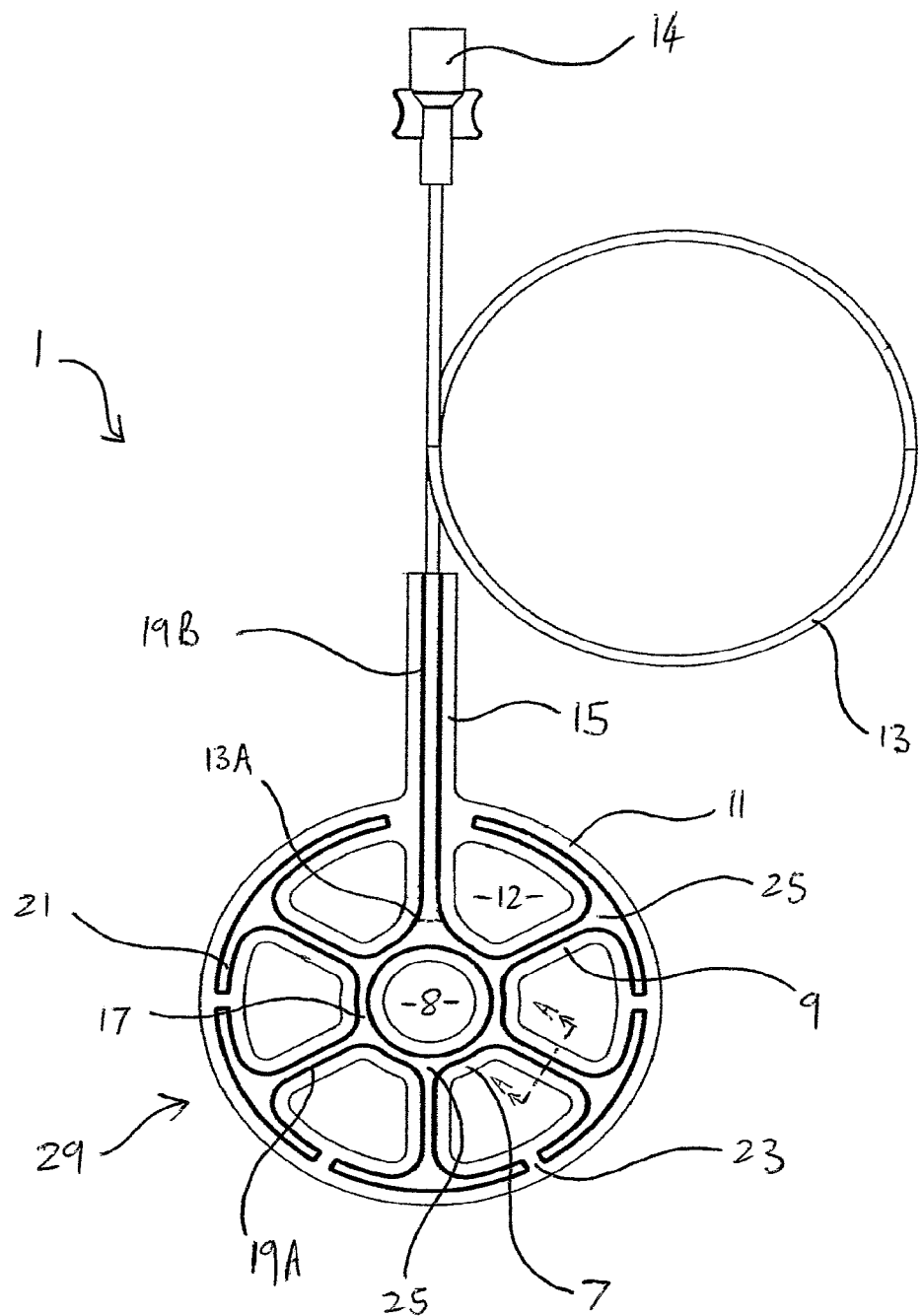
FIG. 1 is a top view of an oxygen distributor, in the form of an oxygen distribution web according to an embodiment of the invention.
Figure 2:
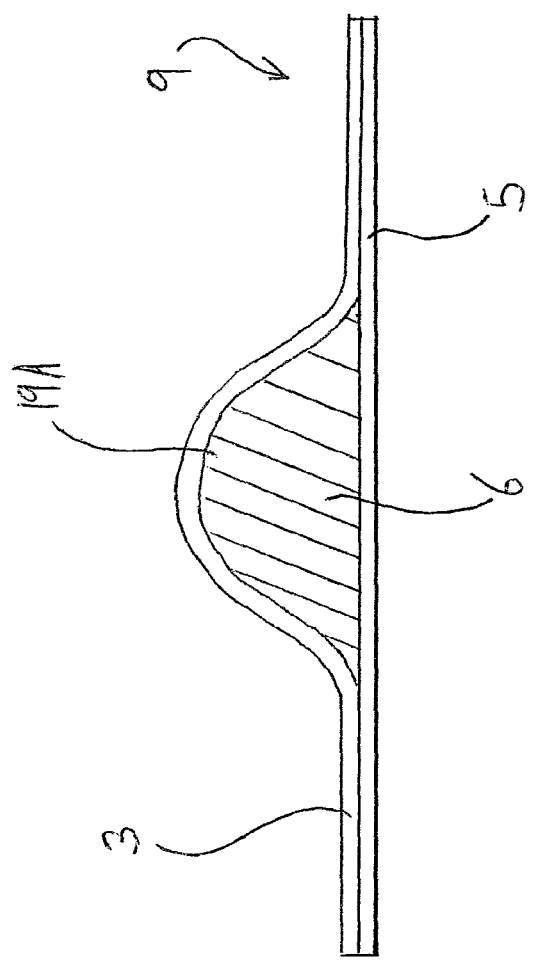
FIG. 2 is a vertical section, on A-A, of the oxygen distribution web of FIG. 1.
Figure 3:
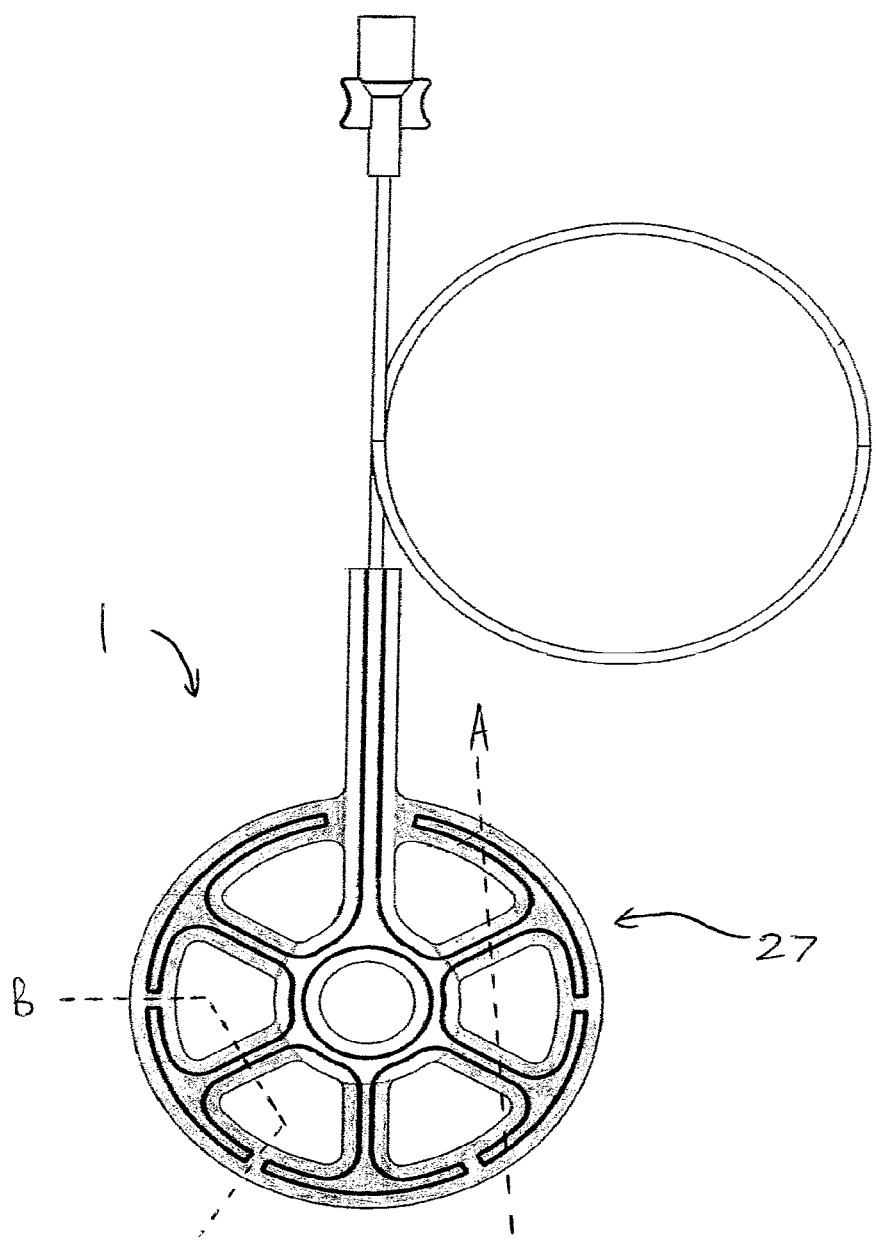
FIG. 3 is a plan view of the oxygen distribution web in FIG. 1, showing the cutting area.

An oxygen distributor in the form of a web 1 according to an embodiment of the invention is shown in FIGS. 1-3. An upper, oxygen-impermeable, liquid-impermeable layer 3 manufactured from co-extruded EVA/PVDC (NEXCEL® MF513) and a lower, oxygen-permeable, liquid-impermeable layer 5 manufactured from polyurethane porous film (TREDEGAR® BF519W) are cut to shape and sealed together in tracks to form strands of the web. Specifically, there is a central, inner track 7 in the form of a ring, six straight radial tracks or spokes 9 extending from the inner track, an outer, circumferential track 11, and a single straight track in the form of a tab 15 which protrudes outwardly from the circumferential track, aligned with one of the six radial tracks. The inner track defines a central exudate hole 8, and a further six exudate holes 12 are defined between the inner track, radial tracks and circumferential track. The circumferential track defines an outer edge of an oxygen distribution portion 29 of the web.

Defined within the inner track 7 is an oxygen delivery area or manifold 17 in the form of a ring-shaped oxygen delivery tube. Emanating from the oxygen delivery area are five, radial tubes 19A, defined in five of the six radial tracks 9. Each of the five radial tubes branches to form a circumferential or branching tube 21 defined within the circumferential track 11. Each of the five radial tubes and their connected circumferential tubes forms an independent sub-network of tubes which, except at the oxygen delivery area, are not interlinked to other sub-networks. The circumferential tubes of neighbouring sub-networks are separated from each other by sealed portions 23 of the circumferential track, which create closed ends in the circumferential tubes. Nevertheless the circumferential track physically restrains the closed tube ends in the plane of the distributor.

A long, straight radial tube 19B is defined in one of the radial tracks 9, across the circumferential track 11 and along the tab 15. This tube does not branch to form a circumferential tube. Rather, it extends from the oxygen delivery area 17 to the outer edge of the tab 15.

FIG. 2 shows a cross section of one of the radial tracks 9 with one of the radial tubes 19A defined within it. On each side of the tube, the oxygen-impermeable, liquid-impermeable layer 3 is sealed to the oxygen-permeable, liquid-impermeable layer 5.

Each tube 17, 19A, 21 is defined between the oxygen-impermeable, liquid-impermeable layer 3 and the oxygen-permeable, liquid-impermeable layer 5. Porous material in the form of polyurethane open cell foam 6 (CORPURA® MCF03) is distributed within each tube. The porous material is shown specifically in FIG. 3.

An oxygen delivery means 13, in the form of a plastics conduit (liquid-impermeable and gas-impermeable) is positioned and sealed at one end within the long radial tube 19B. The oxygen delivery means has a delivery end 13A which is positioned at the oxygen delivery area 17. At its opposite end the oxygen delivery means has a connecting end 14 for connecting to an oxygen supply.

For most of their length, each tube 17, 19A, 21 has a width of 1.5 to 2 mm. This is a minimum width of the tube. Where the tubes intersect to form junctions 25, the width may be greater than this and is about 4 to 5 mm. Each tube has a maximum height of approximately 1 to 2 mm.

The maximum cross-sectional area of each tube is approximately 5 mm$^2$ but for most of the length of each tube, where the tube has a minimum width, the cross-sectional area is approximately 1.5-3 mm$^2$.

The short radial tubes 19A have a length of approximately 15 mm and the long radial tube 19B has a length of approximately 50 mm, with the distance between the outer edge of the tab 15 and the delivery end 13A of the oxygen delivery means being approximately 46 mm.

The diameter of the oxygen delivery web 1 defined between outer edges of the circumferential track 11 is approximately 60 mm.

A cutting area 27 as shown by the shaded part in FIG. 3, is defined between the inner track 7 and the outer edge of the outer, circumferential track 11.

The circumferential track defines the outer edge of an oxygen distribution portion 29 of the web, for delivering oxygen to a wound, which excludes the tab 15 and the oxygen delivery means 13.

In use, the oxygen delivery means 13 is connected to an oxygen supply (not shown) and the oxygen distribution portion 29 of the web 1 is placed in a wound (not shown). A wound dressing such as an absorbent dressing, a gauze and/or compression bandage (not shown) is placed over the web. Oxygen at a pressure greater than atmospheric pressure is fed from the oxygen supply through the oxygen delivery means 13 to the oxygen delivery area 17. Oxygen is able to pass from the oxygen delivery area through each of the short radial tubes 19A, towards the periphery of the web and through each circumferential tube 21. As the oxygen passes through the oxygen delivery area, through each short radial tube and through each circumferential tube, it is able to permeate through the oxygen-permeable, liquid-impermeable layer 5 to the wound, thus distributing oxygen across the wound surface and increasing a concentration of oxygen at the wound site.

Wound exudate produced at the wound site is able to pass through the exudate holes 8, 12 and away from the wound site. Typically, an absorbent dressing is placed over the web 1 to protect the wound and absorb exudate which has passed through the exudate holes.

In certain circumstances, for example when dealing with small wounds, it is desirable to cut the web 1 to reduce its area. If this is required, cutting takes place in the predetermined cutting area 27.

The tubes in the cutting area are arranged such that if a single straight cut is made across the cutting area 27 to reduce the area of the web, no more than four tubes can be cut across, and no more than two short radial tubes 19A are cut across. An example of a possible single, straight cut, cutting across a total of four tubes (including only two short radial tubes 19A) is shown by line A in FIG. 3.

FIG. 3 also demonstrates how a significant area of the web can be cut whilst only cutting across one tube. Line B shows how the dressing can be cut across two of the sealed areas 23 in the circumferential track 11 and across one of the radial tracks 9 such that only one short radial tube 19A is cut across. Only one sub-network is therefore affected by the cutting.

Example

Oxygen Distribution Web Performance in Raising and Maintaining an Oxygen Enriched Headspace
Apparatus:
  Oxygen distribution web (as shown in FIGS. 1 to 3 above).
  Perspex® slab pre-drilled to house the oxygen delivery web.
  Alphasense® Ltd Oxygen sensor calibrated each evaluation (Alphasense Ltd supply the sensor calibrated for use in air and specifically designed for use in safety critical portable instruments used by those subject to life threatening oxygen levels in their work place).
  Digital Volt Meter (DVM) (serial No 1100391805) set to display milliamp (mA) current.
  A disc of hydrophobic, gas-permeable material sold under the trade mark Tredegar® (equivalent to the lower, gas-permeable, liquid-impermeable layer of the oxygen distribution web).
  Natrox™ oxygen supply device (serial No 110212-35)—For supplying a continuous flow (12 ml/hr) of humidified oxygen.
  Gauze pad—Crest Medical 8 ply.
  A single layer compression bandage.
  2 ml of Synthetic exudate (5% Xanthum Gum with water).

The oxygen sensor is configured to monitor oxygen concentration in air. Atmospheric oxygen (21%) produces a signal of ~0.097 mA. This signal increases in proportion to the oxygen concentration present at the sensor surface.
Method:
The oxygen sensor is mounted flush with the surface of a Perspex® fixture. To protect the sensor from exudate, the disc of Tredegar® hydrophobic material is placed over the sensor and sealed using tape. Synthetic exudate is smeared on the Tredegar® surface and the oxygen delivery web is placed on this, followed by gauze and finally the single layer compression bandage. The sensor is calibrated in air and the Natrox™ oxygen supply is connected to the oxygen distribution web. The time is noted and periodic readings are taken.

CONCLUSIONS

A DVM reading of 0.147 mA corresponds to an oxygen concentration of 29.76% at the 'wound surface', and this is achieved within 3 hours of connection to the Natrox™ oxygen supply.

Figure 4:
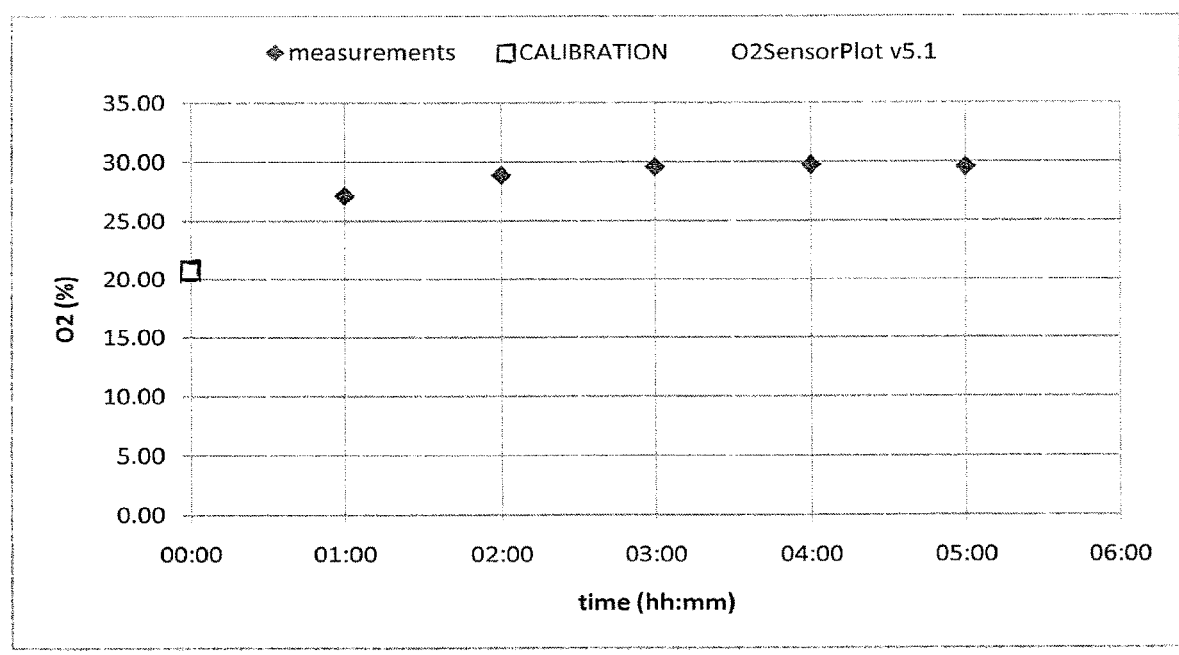
FIG. 4 is a graph showing an increase in oxygen concentration at a simulated wound site, using the oxygen distribution web of FIGS. 1 to 3.

Therefore, the dressing combination above led to an approximate 50% rise in oxygen concentration at the 'wound' surface, which was maintained until the experiment terminated after 5 hours (See FIG. 4).

The invention claimed is:
1. An oxygen distributor to supply oxygen to a wound, the oxygen distributor comprising:
  an oxygen delivery area to receive a supply of oxygen; and
  a plurality of tubes in fluidic communication with the oxygen delivery area, each of the plurality of tubes having a tube wall, wherein the tube wall of at least one of the plurality of tubes includes an oxygen-permeable, liquid-impermeable section, and wherein there is at least one open region defined between or among the plurality of tubes to enable exudate from the wound to flow away from the wound,
  the at least one of the plurality of tubes arranged such that oxygen delivered to the oxygen delivery area flows away from the oxygen delivery area along the at least one of the plurality of tubes for delivery to the wound via the oxygen-permeable, liquid-impermeable section.
2. The oxygen distributor of claim 1, wherein at least one of the plurality of tubes is curved.
3. The oxygen distributor of claim 1, wherein at least one of the plurality of tubes is substantially straight.
4. The oxygen distributor of claim 1, wherein the plurality of tubes comprise at least one substantially straight tube and at least one curved tube.
5. The oxygen distributor of claim 1, wherein the oxygen delivery area comprises a delivery tube.

6. The oxygen distributor of claim 5, wherein the plurality of tubes extend from different positions around or along the length of the delivery tube.

7. The oxygen distributor of claim 1, wherein the tube wall of at least one of the plurality of tubes further includes an oxygen-impermeable, liquid-impermeable section.

8. The oxygen distributor of claim 1, wherein the tube wall of each of the plurality of tubes is liquid-impermeable.

9. The oxygen distributor of claim 1, wherein each of the plurality of tubes has a tube wall including an oxygen-permeable, liquid-impermeable section, and wherein at least some of the plurality of tubes have closed ends.

10. The oxygen distributor of claim 1, wherein the at least one open region is defined between two tubes of the plurality of tubes.

11. The oxygen distributor of claim 1, wherein the at least one open region is defined between two tubes of the plurality of tubes, wherein the two tubes extend radially from the oxygen delivery area.

12. The oxygen distributor of claim 1, wherein the at least one open region comprises at least 50% of the total area of the oxygen distributor, the total area being defined by the perimeter of the oxygen distributor.

13. The oxygen distributor of claim 1, where the oxygen distributor is substantially rectangular in shape.

14. An oxygen distributor to supply oxygen to a wound, comprising:
  an oxygen delivery area to receive a supply of oxygen;
  a curved tube in fluidic communication with the oxygen delivery area and having a tube wall, wherein the tube wall includes an oxygen-permeable, liquid-impermeable section, and wherein the curved tube surrounds an open region that enables exudate from the wound to flow away from the wound,
  the tube arranged such that oxygen delivered to the oxygen delivery area flows away from the oxygen delivery area along the tube for delivery to the wound via the oxygen-permeable, liquid-impermeable section.

15. The oxygen distributor of claim 14, wherein the curved tube extends to a peripheral edge of the oxygen distributor.

16. The oxygen distributor of claim 14, where the oxygen distributor is substantially circular in shape.

17. The oxygen distributor of claim 14, wherein the open region comprises at least 50% of the total area of the oxygen distributor, the total area being defined by the perimeter of the oxygen distributor.

18. The oxygen distributor of claim 14, wherein the open region comprises at least 60% of the total area of the oxygen distributor, the total area being defined by the perimeter of the oxygen distributor.

19. The oxygen distributor of claim 14, wherein the tube wall further includes an oxygenimpermeable, liquid-impermeable section.

20. The oxygen distributor of claim 14, wherein the tube wall is liquid-impermeable.

* * * * *